United States Patent
Hoess et al.

(10) Patent No.: US 6,858,410 B2
(45) Date of Patent: Feb. 22, 2005

(54) PROCESS FOR MAKING ANTIFUSOGENIC FUSION PEPTIDES THAT FORM INCLUSION BODIES

(75) Inventors: Eva Hoess, Munich (DE); Thomas Meier, Munich (DE); Gabriele Pestlin, Munich (DE); Friedrich Popp, Penzberg (DE); Klaus Reichert, Weilheim (DE); Rainer Schmuck, Benediktbeuern (DE); Bernd Schneidinger, Hohenschaeftlarn/Neufahrn (DE); Christoph Seidel, Weilheim (DE); Wilhelm Tischer, Peissenberg (DE)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/158,742

(22) Filed: May 30, 2002

(65) Prior Publication Data

US 2003/0104581 A1 Jun. 5, 2003

(30) Foreign Application Priority Data

Jun. 15, 2001 (EP) .............................. 01114497

(51) Int. Cl.[7] .......................... C12P 21/00; A61K 38/00
(52) U.S. Cl. .................. 435/71.1; 435/71.2; 424/184.1; 424/192.1; 530/300; 530/350
(58) Field of Search .......................... 424/184.1, 192.1; 435/71.1, 71.2; 530/350, 300

(56) References Cited

U.S. PATENT DOCUMENTS

| | | | |
|---|---|---|---|
| 4,511,503 A | 4/1985 | Olson et al. | |
| 5,453,363 A | 9/1995 | Rudolph et al. | |
| 5,464,933 A | 11/1995 | Bolognesi et al. | |
| 5,635,371 A | 6/1997 | Stout et al. | |
| 5,656,456 A | 8/1997 | Stout et al. | |
| 5,656,480 A | 8/1997 | Wild et al. | |
| 5,830,634 A | 11/1998 | Brust et al. | |
| 6,013,263 A | 1/2000 | Barney et al. | |
| 6,017,536 A | 1/2000 | Barney et al. | |
| 6,060,065 A | 5/2000 | Barney et al. | |
| 6,093,794 A | 7/2000 | Barney et al. | |
| 2001/0009667 A1 | 7/2001 | Burst et al. | |
| 2002/0123039 A1 | 9/2002 | Burst et al. | |

FOREIGN PATENT DOCUMENTS

| | | |
|---|---|---|
| CA | WO 94/04688 A2 * | 3/1994 |
| DE | 30 34 045 | 4/1982 |
| EP | 0416673 | 3/1991 |
| EP | 424 990 | 5/1991 |
| EP | 0673948 | 9/1995 |
| WO | WO 92/01707 | 2/1992 |
| WO | WO 94/01451 | 1/1994 |
| WO | WO 95/03405 | 2/1995 |
| WO | WO 96/19495 | 6/1996 |
| WO | WO 96/40191 | 12/1996 |
| WO | WO 99/09179 | 2/1999 |
| WO | WO 99/48513 | 9/1999 |
| WO | WO 99/59615 | 11/1999 |

(List continued on next page.)

OTHER PUBLICATIONS

Lu, M. et al, Nature Structural Biology, 2(12), (1995) pp. 1075–1082.

(List continued on next page.)

*Primary Examiner*—James Housel
*Assistant Examiner*—Stacy B. Chen
(74) *Attorney, Agent, or Firm*—George W. Johnston; Dennis P. Tramaloni; Samuel H. Megerditchian (57) ABSTRACT

A process is provided for producing an antifusogenic peptide by producing a fusion peptide of from about 14 amino acids up to 70 amino acids in a prokaryotic host cell under conditions in which inclusion bodies are formed. The antifusogenic peptide recovered from the inclusion bodies is a fragment cleaved from the fusion peptide which comprises an antifusogenic peptide.

5 Claims, 1 Drawing Sheet

FOREIGN PATENT DOCUMENTS

| WO | WO 00/03011 | 1/2000 |
|----|-------------|--------|
| WO | WO 00/31279 | 6/2000 |
| WO | WO 00/69902 | 11/2000 |
| WO | WO 01/44286 | 6/2001 |
| WO | WO 02/103026 | 12/2002 |

OTHER PUBLICATIONS

Marston Fao, Biochem. J., 240(1), (1986) pp. 1–12.

Chan et al., Proc. Natl. Acad. Sci. USA, 95, pp. 15613–15617 (1998).

Chen et al. J. Virol, 69, pp. 3771–3777 (1995).

Döbeli et al., Protein Expression and Purification, 12, pp. 404–414 (1998).

Judice et al., Proc. Natl. Acad. Sci. USA, 94, pp. 13426–13430 (1997).

Lambert et al., Proc. Natl. Acad. Sci. USA, 93, pp. 2186–2191 (1996).

Lilie, H., Curr. Opin. Biotechnol., 9, pp. 497–501 (1998).

Mergler et al., Tetrahedron Letters, 29, pp. 4005–4008 (1988).

Mergler et al., Tetrahedron Letters, 29, pp. 4009–4012 (1988).

Tan et al., Proc. Natl. Acad. Sci. USA, 94, pp. 12303–12308 (1997).

Uhlen et al., Gene Fusions For Purposes of Expression, An Introduction in Methods in Enzymology, 185, pp. 129–143, (1990), Academic Press.

Van Heeke et al., Method Mol., Biol., 36, pp. 245–260 (1994).

* cited by examiner

PROCESS FOR MAKING ANTIFUSOGENIC FUSION PEPTIDES THAT FORM INCLUSION BODIES

FIELD OF THE INVENTION

The invention relates to methods for the recombinant production of peptides which inhibit the fusion of viruses with membranes of target cells. In particular, this invention relates to the recombinant production of peptidic inhibitors of lentivirus such as human immunodeficiency virus (HIV), Simian immunodeficiency virus (SIV), measles virus (MEV), influenza viruses such as respiratory syncytical virus (RSV) or human parainfluenza virus (HPV).

BACKGROUND OF THE INVENTION

Fusion of viruses with cellular membranes is an essential step for the entry of enveloped viruses, such as HIV-I, HIV-II, RSV, measles virus, influenza virus, parainfluenza virus, Epstein-Barr virus and hepatitis virus, into cells. After having entered the cell the cascade of viral replication may be initiated resulting in viral infection.

HIV is a member of the lentivirus genus, which includes retroviruses that possess complex genomes and exhibit cone-shaped capsid core particles. Other examples of lentiviruses include the simian immunodeficiency virus (SIV), visna virus, and equine infectious anemia virus (EIAV). Like all retroviruses, HIV's genome is encoded by RNA, which is reverse-transcribed to viral DNA by the viral reverse transcriptase (RT) upon entering a new host cell. Influenza viruses and their cell entry mechanisms are described by Bullough, P. A., et al., Nature 371 (1994) 37–43; Carr, C. M., and Kim, P. S., Cell 73 (1993) 823–832; and Wilson, I. A., et al., Nature 289 (1981) 366–373.

All lentiviruses are enveloped by a lipid bilayer that is derived from the membrane of the host cell. Exposed surface glycoproteins (SU, gp120) are anchored to the virus via interactions with the transmembrane protein (TM, gp41). The lipid bilayer also contains several cellular membrane proteins derived from the host cell, including major histocompatibility antigens, actin and ubiquitin (Arthur, L. O., et al., Science 258 (1992) 1935–1938). A matrix shell comprising approximately 2000 copies of the matrix protein (MA, p17) lines the inner surface of the viral membrane, and a conical capsid core particle comprising ca. 2000 copies of the capsid protein (CA, p24) is located in the center of the virus. The capsid particle encapsidates two copies of the unspliced viral genome, which is stabilized as a ribonucleoprotein complex with ca. 2000 copies of the nucleocapsid protein (NC, p7), and also contains three essential virally encoded enzymes: protease (PR), reverse transcriptase (RT) and integrase (IN). Virus particles also package the accessory proteins, Nef, Vif and Vpr. Three additional accessory proteins that function in the host cell, Rev, Tat and Vpu, do not appear to be packaged.

In the case of HIV, viral entry is associated with the HIV envelope surface glycoproteins (Lawless, M. K., et al., Biochemistry 35 (1996) 13697–13708; and Turner, B. G., and Summers, M. F., J. Mol. Biol. 285 (1999) 1–32). In the case of HIV-I, this surface protein is synthesized as a single 160 kD precursor protein, which is cleaved by a cellular protease into two glycoproteins gp-41 and gp-120. gp-41 is a transmembrane protein, and gp-120 is an extracellular protein which remains non-covalently associated with gp-41 in a trimeric or multimeric form (Hammarskjöld, M.-L., et al., Biochim. Biophys. Acta 989 (1989) 269–280). HIV is targeted to $CD4^+$ lymphocytes because the CD4 surface protein acts as the cellular receptor for the HIV-I virus. Viral entry into cells is dependent upon gp-120 binding to the cellular $CD4^+$ receptor molecules while gp-41 anchors the envelope glycoprotein complex in the viral membrane and mediates membrane fusion (McDougal, J. S., et al., Science 231 (1986) 382–385; and Maddon, P. J., et al., Cell 47 (1986) 333–348).

gp41 is the transmembrane subunit that mediates fusion of viral and cellular membranes. The gp41 ectodomain core is a six-helix bundle composed of three helical hairpins, each consisting of an N helix paired with an antiparallel C helix (Chan, D. C., et al., Cell 89 (1997) 263–273; Weissenhorn, W., et al., Nature 387 (1997) 426–430; Tan, K., et al., Proc. Natl. Acad. Sci. USA 94 (1997) 12303–12308). The N helices form an interior, trimeric coiled coil with three conserved, hydrophobic grooves; a C helix packs into each of these grooves. This structure likely corresponds to the core of the fusion-active state of gp41. According to Chan, D. C., et al., Proc. Natl. Acad. Sci. USA 95 (1998) 15613–15617, there is evidence that a prominent cavity in the coiled coil of the HIV type 1 gp41 is an attractive drug target.

It is assumed that the mechanism by which gp-41 mediates membrane fusion may involve the formation of a coiled-coil trimer, which is thought to drive the transition from resting to fusogenic states, as is described, for example, for influenza hemagglutinin (Wilson, I. A., et al., Nature 289 (1981) 366–373; Carr, C. M., and Kim, P. S., Cell 73 (1993) 823–832; Bullough, P. A., et al., Nature 371 (1994) 37–43).

C peptides (peptides corresponding to the C helix) of enveloped viruses, such as DP178 and C34, potently inhibit membrane fusion by both laboratory-adapted strains and primary isolates of HIV-1 (Malashkevich, V. N., et al., Proc. Natl. Acad. Sci. USA 95 (1998) 9134–9139; Wild, C. T., et al., Proc. Natl. Acad. Sci. USA 91 (1994) 9770–9774). A Phase I clinical trial with the C peptide DP178 suggests that it has antiviral activity in vivo, resulting in reduced viral loads (Kilby, J. M., et al., Nature Medicine 4 (1998) 1302–1307). The structural features of the gp41 core suggest that these peptides act through a dominant-negative mechanism, in which C peptides bind to the central coiled coil of gp41 and lead to its inactivation (Chan, D. C., et al., Cell 93 (1998) 681–684).

Within each coiled-coil interface is a deep cavity, formed by a cluster of residues in the N helix coiled coil, that has been proposed to be an attractive target for the development of antiviral compounds. Three residues from the C helix (Trp-628, Trp-631, and Ile-635) insert into this cavity and make extensive hydrophobic contacts. Mutational analysis indicates that two of the N-helix residues (Leu-568 and Trp-571) comprising this cavity are critical for membrane fusion activity (Cao, J., et al., J. Virol. 67 (1993) 2747–2755). Therefore, compounds that bind with high affinity to this cavity and prevent normal N and C helix pairing may be effective HIV-1 inhibitors. The residues in the cavity are highly conserved among diverse HIV-1 isolates. Moreover, a C peptide containing the cavity-binding region is much less susceptible to the evolution of resistant virus than DP178, which lacks this region (Rimsky, L. T., et al., J. Virol. 72 (1998) 986–993). These observations suggest that high-affinity ligands targeting the highly conserved coiled-coil surface, particularly its cavity, will have broad activity against diverse HIV isolates and are less likely to be bypassed by drug-escape mutants.

Fusogenic structures of envelope fusion proteins was shown from influenza, Moloney murine leukemia virus, and simian immunodeficiency virus (cit. in Chan, D. C., Proc. Natl. Acad. Sci. USA 95 (1998) 15613–15617), human respiratory syncytial virus, Ebola, human T cell leukemia virus, simian parainfluenza. It indicates a close relationship between the families of orthomyxoviridae, paramyxoviridae, retroviridae, and others like filoviridae, in which viral entry into target cells is enabled by like transmembrane glycoproteins such as gp41 of HIV-1, hemagglutinin of influenza, GP2 of Ebola and others (Zhao, X., et al., Proc. Natl. Acad. Sci. USA 97 (2000) 14172–14177).

In the state of the art, methods are described for the preparation of peptidic inhibitors (C-peptides) (see, e.g., Root, M. J., et al., Science 291 (2001) 884–888; Root et al. describe peptide C37-H6 which is derived from HIV-1. HXB2 and contains residues 625–661. It was recombinantly expressed as N40-segment with a GGR-linker and a histidine tag, expressed in E. coli and purified from the soluble fraction of bacterial lysates. Zhao, X., et al. describe in Proc. Natl. Acad. Sci. USA 97 (2000) 14172–14177 a synthetic gene of recRSV-1 (human respiratory syncytial virus) which encodes Residues 153–209, a G-rich linker, residues 476–524, Factor Xa cleavage site and a his-tag. Chen, C. H., et al., describe in J. Virol. 67 (1995) 3771–3777 the recombinant expression of the extracellular domain of gp41 synthesized as fusion protein, residues 540–686, fusion to MBP.

A number of peptidic inhibitors, also designated as antifusogenic peptides, of such membrane fusion-associated events are known, including, for example, inhibiting retroviral transmission to uninfected cells. Such peptides are described, for example, by Lambert, D. M., et al., Proc. Natl. Acad. Sci. USA 93 (1996) 2186–2191, in U.S. Pat. Nos. 6,013,263; 6,017,536; and 6,020,459; and in WO 00/69902, WO 99/59615 and WO 96/40191. Further peptides inhibiting fusing associated events are described, for example, in U.S. Pat. Nos. 6,093,794; 6,060,065; 6,020,459; 6,017,536; 6,013,263; 5,464,933; 5,656,480; and in WO 96/19495.

Examples of linear peptides derived from the HIV-I gp-41 ectodomain which inhibit viral fusion are DP-107 and DP-178. DP-107 is a portion of gp-41 near the N-terminal fusion peptide and has been shown to be helical, and it strongly oligomerizes in a manner consistent with coiled-coil formation (Gallaher, W. R., et al., Aids Res. Hum. Retrovirus 5 (1989) 431–440, Weissenhorn, W., et al., Nature 387 (1997) 426–430). DP-178 is derived from the C-terminal region of the gp-41 ecto-domain. (Weissenhorn, W., et al., Nature 387 (1997) 426–430). Although without discernible structure in solution this peptide and constrained analogs therefrom adopt a helical structure, bind to a groove of the N-terminal coiled-coil trimer of gp41 and thus prevent the gp41 to transform into the fusogenic state (Judice, J. K., et al., Proc. Natl. Acad. Sci. USA 94 (1997) 13426–13430).

Such short-chain peptides usually are prepared by chemical synthesis. Chemical synthesis is described, for example, by Mergler, M., et al., Tetrahedron Letters 29 (1988) 4005–4008 and 4009–4012; Andersson, L., et al., Biopolymers 55 (2000) 227–250; and by Jones, J. H., J. Pept. Sci. 6 (2000) 201–207. Further methods are described in WO 99/48513.

However, chemical peptide synthesis suffers from several drawbacks. Most important is racemization, which results in insufficient optical purity. In peptide chemistry, racemization also means epimerization at one of several chirality centers. If only 1% racemization occurs for a single coupling step, then at 100 coupling steps only 61% of the target peptide would be received (Jakubke, H. D., Peptide, Spektrum Akad. Verlag, Heidelberg (1996), p. 198). It is obvious that the number of impurities increases with growing chain length and their removal is more and more difficult and costly.

Chemical synthesis on large scale is limited by high costs and lack of availability of protected amino acid derivatives as starting materials. On the one hand, these starting materials should be used in excess to enable complete reactions, on the other hand, their use should be balanced for cost reasons, safety and environmental aspects (Andersson et al., Biopolymers 55 (2000) 227–250).

Peptides may also be produced by recombinant DNA technology. Whereas recombinant production of soluble proteins of chain lengths of more than 50 amino acids is known from the state of the art, the production of peptides with fewer than 50 amino acids suffers from several drawbacks (Doebeli, H., et al, Protein Expression and Purification 12 (1998) 404–414). Such short or medium chain peptides are usually not stably expressed. They are attacked by intrinsic peptidases and degraded. This may result from their small size or lack of highly ordered tertiary structure (WO 00/31279). Other authors have found that recombinant production of peptides requires a minimum chain length of 60 to 80 amino acids for a stable expression, and it is further common knowledge that such peptides are produced as soluble peptides and not as inclusion bodies (see, e.g., van Heeke, G., et al., Methods in Molecular Biology 36 (1994) 245–260, eds. B. M. Dunn and M. W. Pennington, Humana Press Inc., Totowa, N.J.); and Goldberg et al., Maximizing Gene Expression (1986), pp. 287–314, eds. Reznikoff, W., and Gold, L., Butterworks, Stoneham, Mass.). Recombinant production of shorter peptides is especially not successful because if such peptides are expressed in prokaryotes, they remain soluble and are immediately degraded by prokaryotic peptidases. To avoid this problem, according to common knowledge, such peptides are expressed as large (more than 150 to 200 amino acids) fusion proteins, whereby the fusion tail either renders the fusion protein fairly soluble and avoids the formation of inclusion bodies or the fusion tail is a protein which forms during recombinant expression in prokaryotes, inclusion bodies, and therefore fusion protein consisting of such fusion tail and the desired short peptide will also form inclusion bodies during overexpression in prokaryotes. A great disadvantage of such methods is that the molecular weight of the fusion tail is considerably higher than the molecular weight of the desired peptide. Therefore, the yield of the desired peptide is very low and the excess of cleaved fusion tail has to be separated of.

Lepage, P., et al., in Analytical Biochemistry 213 (1993) 40–48, describe recombinant methods for the production of HIV-1Rev peptides. The peptides are expressed as fusion proteins with the synthetic immunoglobulin type G (IgG) binding domains of Staphylococcus aureus protein A. The peptides have a length of about 20 amino acids, whereas the IgG-binding part has a length of about 170 amino acids, so that the expressed fusion protein has an overall length of about 190 amino acids. This fusion protein is expressed, secreted in soluble form in the medium, and purified by affinity chromatography. The authors reported that with this method it might be possible to produce recombinant protein in an amount of hundreds of milligrams per liter of culture. However, this methodology is limited due to alternative processing within the signal peptide sequence and several post-translational modifications of the fused proteins as well as of the cleaved peptides. Assuming an average molecular weight of an amino acid of 110 Daltons, the desired peptides have a molecular weight of about 2,000 to 5,000 Daltons, whereas the fusion tail has a length of at least 170 amino acids (about 19,000 D), if the IgG binding domains of Staphylococcus aureus protein A is used as such a fusion tail. Therefore, only 10 to 25% of the recombinantly produced protein is the desired peptide.

EP 0 673 948 describes the recombinant production of a gp41 peptide as a fusion protein with β-galactosidase using the expression vector pSEM3 (Knapp, S., et al., BioTechniques 8 (1990) 280–281). This fusion protein contains a large part of β-galactosidase gene, encoding the N-terminal 375 amino acids and additional 23 codons of a polylinker sequence.

Further examples and methods for the recombinant production of small peptides via large fusion proteins in E. coli are described by Uhlen and Moks, "Gene Fusions For Purposes of Expression, An Introduction" in Methods in Enzymology 185 (1990) 129–143, Academic Press. In regard to the production via the "inclusion body" way, Uhlen and Moks refer to large fusion products involving fusion parts like trpE, cII and again β-galactosidase. Ningyi, L., et al., Gaojishu Tongxun 10 (2000) 28–31 describe the recombinant expression of p24 gag gene in E. coli.

SUMMARY OF THE INVENTION

The present invention provides a process for the production of an antifusogenic peptide by producing a fusion peptide of a length of about 14 to 70 amino acids in a prokaryotic host cell, comprising the steps, under such conditions that inclusion bodies of said fusion peptide are formed, of:
a) expressing in said host cell a nucleic acid encoding said fusion peptide consisting of a first peptide which is an antifusogenic peptide of a length of about 10 to 50 amino acids and a second peptide of a length of about 4 to 30 amino acids, said first peptide being N-terminally linked to said second peptide;
b) cultivating said host cell to produce said inclusion bodies; and
c) recovering said antifusogenic peptide from said inclusion bodies, wherein said recovered antifusogenic peptide consists of said fusion peptide or a peptide comprising the antifusogenic peptide of about 10 to 50 amino acids resulting from cleavage of said fusion peptide.

The present invention also provides a nucleic acid encoding a fusion peptide of from about 14 to 70 amino acids consisting of a first peptide which is an antifusogenic peptide selected from the group of SEQ ID NO: 7, SEQ ID NO: 8, SEQ ID NO: 9, SEQ ID NO: 10, and said sequences further consisting of glycine at the C terminal end, N-terminally linked to a second peptide consisting of 4 to 30 amino acids.

In addition, the present invention provides a composition comprising inclusion bodies consisting essentially of at least one fusion peptide of from about 14 to 70 amino acids consisting of a first peptide which is an antifusogenic peptide selected from the group of SEQ ID NO: 7, SEQ ID NO: 8, SEQ ID NO: 9, SEQ ID NO: 10, and said sequences further consisting of glycine at the C terminal end, N-terminally linked to a second peptide consisting of 4 to 30 amino acids, and optionally at least one peptide comprising the antifusogenic peptide of from about 10 to 50 amino acids and which is a fragment of said fusion peptide.

It is an object of the present invention to provide a method for the recombinant production of a high yield of antifusogenic peptides via the inclusion body route. It is also an object of the invention to provide such a method which is suitable for the large-scale industrial production of antifusogenic peptides.

BRIEF DESCRIPTION OF THE SEQUENCES

SEQ ID NO:1 Synthetic gene Xa-T 1357.
SEQ ID NO:2 Peptide Xa-T1357.
SEQ ID NO:3 Primer 1.
SEQ ID NO:4 Primer 2.
SEQ ID NO:5 Primer 3.
SEQ ID NO:6 Primer 4.
SEQ ID NO:7 Peptide T1357.
SEQ ID NO:8 Peptide T680.
SEQ ID NO:9 Peptide RSV118.
SEQ ID NO:10 Peptide MV257.
SEQ ID NO:11 Peptide Xa-RSV118.
SEQ ID NO:12 Peptide Xa-MV257.
SEQ ID NO:13 Peptide M-HHHHHH-AIDV-IEGR-T1357-G.
SEQ ID NO:14 Peptide M-HHHHHH-IEGR-T1357-G.
SEQ ID NO:15 Peptide M-HHHHHH-IEGR-T680-G.
SEQ ID NO:16 Cleavage sequence.
SEQ ID NO:17 Cleavage sequence.
SEQ ID NO:18 Cleavage sequence.
SEQ ID NO:19 Cleavage sequence.

DETAILED DESCRIPTION OF THE INVENTION

The present invention provides a process for the production of an antifusogenic peptide as a fusion peptide of a length of about 14 to 70 amino acids in a prokaryotic host cell, characterized in that, under such conditions that inclusion bodies of said fusion peptide are formed,
a) in said host cell there is expressed a nucleic acid encoding said fusion peptide consisting of said antifusogenic peptide of a length of about 10 to 50 amino acids N-terminally linked to a further peptide of a length of about 4 to 30 amino acids;
b) said host cell is cultivated;
c) said inclusion bodies are formed, recovered and solubilized;
d) said fusion peptide is isolated.

Preferably said antifusogenic peptide is cleaved off from said further peptide during or after solubilization of the inclusion bodies.

Preferably, the antifusogenic peptide is a fragment of the C helix of a transmembrane subunit of an envelope fusion protein from a virus of the lentivirus genus.

Said further peptide, if expressed recombinantly in said host cell as a non-fusion peptide, would not be found in the form of inclusion bodies since it is very short.

In a preferred embodiment of the invention, the further peptide consists of a first and/or second part,
(a) wherein said first part is a stretch of from 1 to 20 amino acids, preferably hydrophilic amino acids influencing the isoelectric point of the fusion peptide, and/or said first part differing significantly from the antifusogenic peptide with regard to solubility, interactions with chromatographic separation resins and/or improves access of cleavage proteases (Polyak, S. W., et al., Protein Eng. 10 (1997) 615–619) and
(b) wherein said second part is a cleavable peptidic linker region from 1 to 10 amino acids (see, e.g., Table 3) and is located adjacent to the N-terminus of the fusogenic peptide and the C-terminus of the first part.

If the further peptide consists only of the first or the second part, said part has a length of at least 4 amino acids (including start codon coded methionine) preferably for the purpose of stabilizing during expression mRNA. Said 4 amino acids include preferably at least one arginine.

In a further embodiment of the invention, the antifusogenic peptide contains a glycine attached to its C-terminus. This glycine is useful for the purpose of enzymatic C-terminal amidation.

In a preferred embodiment of the invention, the ratio of the molecular weight of the antifusogenic peptide to the molecular weight of the further peptide in the fusion peptide is 10:1 to 1:2.

Further preferred embodiments of the invention comprise a prokaryotic expression vector containing a nucleic acid encoding a fusion peptide according to the invention and its use for the recombinant production of said peptides.

Preferred embodiments of the invention include a preparation of inclusion bodies of a fusion peptide according to the invention and methods for the production of such inclusion bodies.

A further preferred embodiment of the invention is a nucleic acid which encodes a fusion peptide according to the invention.

level of fusion events between two or more structures, e.g., cell membranes or viral envelopes or pili relative to the level of membrane fusion which occurs between the structures in the absence of the peptide. Examples hereof are peptidic inhibitors of lentiviruses such as human immunodeficiency virus (HIV), respiratory syncytical virus (RSV), human parainfluenza virus (HPV), measles virus (MEV), and Simian immunodeficiency virus (SIV). Such antifusogenic peptides are derived from C helix of a transmembrane subunit of an envelope fusion protein from a virus of the lentivirus genus and bind to the central coiled coil of the transmembrane subunit of the respective virus.

Especially preferred are HIV-1 antifusogenic peptides. Table 1 describes examples of HIV-1 antifusogenic peptides derived from the C-peptide of gp41. These antifusogenic peptides and fragments thereof are particularly useful in the invention.

TABLE 1

| Name* | Name | Amino acid sequence (one-letter code) | SEQ ID NO: |
|---|---|---|---|
| T-1249 | T1357[1) | WQEWEQKITALLEQAQIQQEKNEYELQKLDKWASLWEWF | 7 |
| T-20, | T680[2) | YTSLIHSLIEESQNQQEKNEQELLELDKWASLWNWF | 8 |
| T-118 | RSV118[3) | FDASISQVNEKINQSLAFIRKSDELLHNVNAGKST | 9 |
| T-257 | MV257[3) | LHRIDLGPPISLERLDVGTNLGNAIAKLEDAKELL | 10 |

*for N-terminally acetylated and/or C-terminally amidated peptide; T-20 (synonymous with DP178) and T-1249 are from human immunodeficiency virus type 1 (HIV-1), T-118 is from respiratory syncytial virus (RSV) and T-257 is from measles virus (MV)
[1)]WO 99/59615
[2)]Rimsky, L. T., et al., J. Virol. 72 (1998) 986–993
[3)]Lambert, D. M., Proc. Natl. Acad. Sci. USA 93 (1996) 2186–2191

It was surprisingly found that short-chain antifusogenic peptides (preferably of a length of 10 to 50, more preferably of a length of 10 to 40 amino acids) can be expressed successfully as short fusion peptides of a length of up to 70 amino acids in prokaryotes such as E. coli via the inclusion body route.

According to the invention, a fusion peptide consisting of an antifusogenic peptide N-terminally linked to a further peptide is overexpressed in prokaryotes under conditions, whereby insoluble protein inclusion bodies are formed. Inclusion bodies are found in the cytoplasm if an expression vector which does not contain a signal sequence is used, which otherwise might enable soluble secretion of the protein into the periplasm or the medium. These inclusion bodies are separated from other cell components, for example by centrifugation after cell lysis. The inclusion bodies are solubilized by denaturing agents such as guanidine hydrochloride, urea, substances such as arginine, or strong bases such as KOH or NaOH. After solubilization, such proteins usually have to be refolded by dilution or by dialysis. As the fusion peptide produced according to the method of the invention is a short-chain peptide without disulfide bridges, renaturation is not necessary. After solubilization, the solution conditions, such as the pH, etc. are simply modified in such a way that cleavage of the further peptide is possible, and cleavage is performed if requested. The fusion peptide or antifusogenic peptide can then be recovered from this solution in a simple fashion, for example by size exclusion chromatography, ion exchange chromatography or reverse phase chromatography.

"Antifusogenic" and "anti-membrane fusion" as used herein refer to a peptide's ability to inhibit or reduce the The further peptide according to the invention is a peptide which is added N-terminally to the antifusogenic peptide not for purposes of improving the formation of inclusion bodies. Its purpose is to, for example, improve expression mRNA stabilization, purification (e.g. a His-tag; see, e.g., Zhang, J.-H., et al., Nanjing Daxue Xuebao, Ziran Kexue 36(4) (2000) 515–517) or to allow subsequent N-terminal modification like acetylation or PEGylation.

The further peptide according to the invention is a short peptidic stretch consisting of at least four amino acids (methionine and three further amino acids for cleavage mRNA stabilization and/or expression purposes) to about 30 amino acids preferably to about 20 amino acids (with regard to the nucleic acid codons level). The length of the further peptide is not critical for the invention as long as this peptide is a peptide which would be formed in soluble form in the cytoplasm during recombinant expression in prokaryotes under conditions where large proteins such as immunoglobulins, streptavidin or tissue-type plasminogen activator are produced as inclusion bodies. However, it is preferred that the further peptide is very short for improving the yield of the antifusogenic peptide. (If the ratio of length of further peptide to antifusogenic peptide is 3:1, the amount of antifusogenic peptide in relation to the amount of the fusion peptide recovered is about 50% lower than if the ratio is 1:1 if the same amount of fusion peptide is produced.) The length of the further peptide is selected such that the total length of the fusion peptide does not exceed about 70 amino acids, preferably 50 and most preferably 40 amino acids, for reasons of obtaining acceptable yields of antifusogenic peptides. Therefore, it is especially preferred that the further peptide consists only of an appropriate cleavage site, of some amino acids for improving expression and solubility of the fusion peptide, facilitating the solubilization process of its inclusion bodies or to improve access of cleavage proteases (avoidance of steric hindrance) and/or of some amino acids such as a His-tag for purification means (Hengen, P., Trends Biochem. Sci. 20 (1995) 285–286) and methionine necessary and encoded by the start codon.

The further peptide is a short-chain peptide which, if overexpressed alone in prokaryotes such as *E. coli* and without a signal sequence, would not be formed as inclusion bodies but remains soluble in the cytoplasm or is rapidly degraded in the cytoplasm. Such proteins do not form a fixed denatured tertiary structure, therefore they cannot form a fixed tertiary structure which is poorly soluble, therefore remain soluble and would be degraded by *E. coli* proteases if expressed.

The further peptide according to the invention consists preferably of amino acids which do not form a fixed tertiary conformation which might sterically hinder access of the cleavage agent to the cleavage site between the antifusogenic peptide and the further peptide. For this reason, the further peptide is preferably free of cysteine residues. Cysteine contains a sulfhydryl or thiol group which is highly reactive and can form disulfide bonds. The presence of cysteine can work against the desired lack of fixed secondary or tertiary conformation of the further peptide and therefore its use is avoided.

In a preferred embodiment of the present invention, the N-terminally attached further peptide stretch contains a sequence at its C-terminus, which is cleavable easily by enzymatic or chemical means.

The further peptide according to the invention is used in the fusion peptide also preferably for protection of the N-terminus of the antifusogenic peptide during expression, solubilization, purification and peptide modification. Such fusion peptides are especially valuable in a process for the production of N-terminally modified antifusogenic peptides. Such a method involves forming the recombinant polypeptide as a fusion peptide, which fusion part protects the N-terminus. The recombinant fusion peptide can then be reacted with up to three chemical protecting agents to selectively protect reactive side-chain groups and thereby prevent side-chain groups from being modified. Then the fusion peptide is cleaved with at least one cleavage reagent between the peptide and the fusion part to form an unprotected terminal amino acid reactive group. The unprotected terminal amino acid reactive group is modified with at least one chemical modifying agent such as acetic anhydride or acetic N-hydroxysuccinimide ester for N-terminal acetylation. The side-chains are then deprotected to form a N-terminally modified peptide. Such methods are described, for example, in WO 94/01451; U.S. Pat. No. 5,635,371; and U.S. Pat. No. 5,656,456.

The further peptide part preferably has such a structure that it facilitates the purification of the fusion peptide. The further peptide preferably contains for this purpose an "affinity tag" (cf. Pandjaitan, B., et al., Gene 237 (1999) 333–342), such as polyhistidine (about 6 His residues) or the like.

It is preferred to select the further peptide in such a way that its isoelectric point (IP) differs from the IP of the antifusogenic peptide for easy expression and separation of the fragments after cleavage. Table 2 shows IP's of different fusion peptides and the IP's of non-fusion fusogenic peptides T680 and T1357 (nomenclature according to WO 96/40191 and WO 99/59615). Preferably, the IP of the fusion peptide and the antifusogenic portion of the fusion peptide differ by at least about one pH unit, preferably by about 1 to 2 pH units. Such IP shift can preferably performed by basic amino acids and/or histidines contained in the further peptide.

TABLE 2

Calculating the isoelectric points of antifusogenic peptides

| SEQ ID NO: | Sequence[2] | Calculated |
|---|---|---|
| 8 | T680 | 4.13 |
| 15 | M-HHHHHH-IEGR-*T680*-G | 6.13 |
| — | T1249 | 5.1[1] |
| 7 | T1357 | 4.53 |
| 14 | M-HHHHHH-IEGR-*T1357*-G | 6.23 |
| 2 | MRGS-HHHHHH-AIVD-IEGR-*T1357*-G | 6.23 |

[1]Experimentally determined.
[2]Amino acids in one-letter code; inverse parts are peptide names.

In a further preferred embodiment of the invention, the antifusogenic peptide contains a glycine at its C-terminus. This glycine is useful for the purpose of subsequent enzymatic C-terminal amidation (Bradbury, A. F., and Smyth, D. G., Trends Biochem. Sci. 16 (1991) 112–115).

Especially preferred fusion peptides according to the invention are (amino acids in standard one-letter code):

MRGS-HHHHHH-AIDV-IEGR-*T1357*-G,   (SEQ ID NO:2)

MRGS-HHHHHH-AIDV-IEGR-*RSV118*-G   (SEQ ID NO:11)

MRGS-HHHHHH-AIDV-IEGR-*MV257*-G    (SEQ ID NO:12)

M-HHHHHH-AIDV-IEGR-*T680*-G,       (SEQ ID NO:13)

M-HHHHHH-IEGR-*T1357*-G            (SEQ ID NO:14)

said fusion peptides without the poly HIS tag (His 6), or with the first four amino acids of SEQ ID NO:2, 11 or 12 as further peptide in the fusion peptides.

Annotation: The inverse parts are peptide names, and therefore the letters included in these parts do not constitute one-letter codes for amino acids.

There exist a large number of publications which describe the recombinant production of proteins in prokaryotes via the inclusion body route. Examples of such publications are Misawa, S., et al., Biopolymers 51 (1999) 297–307; Lilie, H., Curr. Opin. Biotechnol. 9 (1998) 497–501; Hockney, R. C., Trends Biotechnol. 12 (1994) 456–463.

The fusion peptides according to the invention are overexpressed in prokaryotes. Overexpression without a signal peptide leads to the formation of inclusion bodies. Methionine coded by the start codon and mentioned in the examples above can be cleaved during further processing. General methods for overexpression of proteins in prokaryotes have been well-known in the state of the art for a long time. Examples of publications in the field are Skelly, J. V., et al., Methods Mol. Biol. 56 (1996) 23–53 and Das, A., Methods Enzymol. 182 (1990) 93–112.

Overexpression in prokaryotes means expression using optimized expression cassettes with promoters such as the tac or lac promoter (EP-B 0 067 540). Usually, this can be performed by the use of vectors containing chemical inducible promoters or promoters inducible via shift of temperature. One of the useful promoters for *E. coli* is the temperature-sensitive λPL promoter (cf. EP-B 0 041 767). A further efficient promoter is the tac promoter (cf. U.S. Pat. No. 4,551,433). Such strong regulation signals for prokaryotes such as *E. coli* usually originate from bacteria-challenging bacteriophages (see Lanzer, M., et al., Proc. Natl. Acad. Sci. USA 85 (1988) 8973–8977; Knaus, R., and Bujard, H., EMBO Journal 7 (1988) 2919–2923; for the λT7 promoter Studier, F. W., et al., Methods Enzymol. 185 (1990) 60–89); for the T5 promoter EP 0 186 069).

By the use of such overproducing prokaryotic cell expression systems the fusion peptides according to the invention are produced at levels at least comprising 10% of the total expressed protein of the cell, and typically 30–40%, and occasionally as high as 50%.

"Inclusion bodies" ((IBs) as used herein refers to an insoluble form of polypeptides recombinantly produced after overexpression of the encoding nucleic acid in prokaryotes. This phenomenon is widely known in the state of the art and is reviewed, for example, by Misawa S., and Kumagai, I., Biopolymers 51 (1999) 297–307); Guise, A. D., et al., Mol. Biotechnol. 6 (1996) 53–64; and Hockney et al., Trends Biotechnol. 12 (1994) 456–463.

Solubilization of the inclusion bodies is preferably performed by adding denaturing agents such as urea, guanidine hydrochloride or alkaline solutions of KOH or NaOH (Guise, A. D., et al., Mol. Biotechnol. 6 (1996) 53–64; Fischer, B., et al., Arzneimittelforschung 42 (1992) 1512–1515).

The fusion peptides according to the invention can be cleaved enzymatically after solubilization with a specifically cleaving protease (restriction protease). The proteinase is selected, taking into consideration the amino acid sequence of the antifusogenic peptide to be produced. Care must be taken that, if possible, the recognition/cleavage sequence of the restriction proteinase does not occur in the antifusogenic peptide, and preferably also not in the further peptide, i.e., it should only occur once in the cleavage region (linker region). Suitable specifically cleaving endoproteinase are, for example, Factor Xa, thrombin, subtilisin, BTN variant/ubiquitin protease peptidase, rennin, collagenase, trypsin, chymotrypsin, endoproteinase Lys-C, kallikrein (Carter, P.: In: Ladisch, M. R.; Willson, R. C.; Painton, C. C.; Builder, S. E., eds., Protein Purification: From Molecular Mechanisms to Large-Scale Processes; ACS Symposium Series No. 427, American Chemical Society, pp. 181–193 (1990)), TEV proteinase (Parks, T. D., et al., Anal. Biochem. 216 (1994) 413–417), IgA protease (Pohlner, J., et al., Nature 325 (1987) 458–462), Kex2p proteinase (EP-A 0 467 839) or *S. aureus* V8 proteinase.

In addition to being cysteine-free, the sequence of the further peptide may preferably exploit other design strategies which promote efficient cleavage in the preselected cleavage environment. Particularly if the preselected cleavage agent is an endopeptidase, it is preferred that the further peptide is soluble in aqueous environments. Amino acids having charged side-groups and hydrophilic properties are, therefore, preferably included in the further peptide to promote solubility or any other amino acids which promote the access of cleavage proteases. Such amino acids are, for example, Glu and Asp (anionic), Arg and Lys, and Ser and Thr (neutral, hydrophilic). If arginine is used, it must be taken into account that arginine constitutes the trypsin cleavage site. Therefore, in such cases where the further peptide should contain arginine, trypsin should be avoided as cleaving protease. The use of lysine, too, is subject to limitations. If the peptide has to be N-terminally modified (see above), there may be a need for protecting lysine groups. Therefore, in such cases, it is preferred to avoid lysine in the further peptide.

The cleavage site is typically selected so that it is not contained in the antifusogenic peptide and is preferably contained in the further peptide. Chemical and enzymatic cleavage sites and the corresponding agents used to effect cleavage of a peptide bond close to one of the sites are described, for example, in WO 92/01707 and WO 95/03405.

Examples for cleavage enzymes and the cleavage sequence are described in Table 3 below:

TABLE 3

| Enzyme | Cleavage sequence[1] | SEQ ID NO: |
|---|---|---|
| Enterokinase | DDDDK | 16 |
| Factor Xa | IEGR | 17 |
| Thrombin | RGPR | 18 |
| Ubiquitin | RGG | |
| Rennin | HPFHL-LVY | 19 |
| Trypsin | D or R | |
| Chymotrypsin | F or Y or W | |
| Clostripain | R | |
| S. aureus V8 | G | |

| Chemical cleavage: | |
|---|---|
| Cleavage substance | Cleavage sequence[1] |
| BrCN | M |
| BNPS-skatole | W |
| 5-Nitro-5-thiocyanobenzoate | C |

[1] Amino acid(s) in one-letter code.

Trypsin is preferably used, which specifically cleaves proteins and peptides at the C-terminal end of arginine. Such an enzyme is known, for example, from porcine or bovine pancreas or recombinant yeasts. Trypsin is particularly suitable for producing the desired polypeptides, if the lysine residues are protected and attacked by the enzyme.

The peptide sequence which can be cleaved by an endoproteinase is understood within the sense of the present invention as a short-chain peptide sequence which is preferably composed of 1 to 20 amino acids preferably 1 to 10 amino acids and contains a C-terminal cleavage site for the desired endoproteinase. This further peptide preferably additionally contains a combination of several amino acids (first part) between the N-terminal end and the desired endoproteinase recognition sequence, preferably selected from amino acids Gly, Thr, Ser, Ala, Pro, Asp, Glu, Arg and Lys. An amino acid stretch in which two to eight of these additional amino acids are the negatively charged amino acids Asp and/or Glu is preferably used as the first part.

Cleavage is also possible using BrCN (chemical cleavage) as long as the antifusogenic peptide does not contain methionine.

The fusion peptides are produced by expression of a DNA (nucleic acid sequence) which codes for the peptide in prokaryotes. The expression vector does not contain any elements that would mediate secretion of the fusion peptide into the medium or periplasm (e.g., signal peptides). Therefore, the peptide is formed as insoluble refractile bodies (IP's). DNA encoding the fusion peptide can be produced according to the methods known in the state of the art. It is further preferred to extend the nucleic acid sequence with additional regulation and transcription elements, in order to optimize the expression in the host cells. A DNA that is suitable for the expression can preferably be produced by synthesis. Such processes are familiar to a person skilled in the art and are described for example in Beattie, K. L., and Fowler, R. F., Nature 352 (1991) 548–549; EP-B 0 424 990; Itakura, K., et al., Science 198 (1977) 1056–1063. It may also be expedient to modify the nucleic acid sequence of the peptides according to the invention.

Such modifications are, for example:

- modification of the nucleic acid sequence in order to introduce various recognition sequences of restriction enzymes to facilitate the steps of ligation, cloning and mutagenesis;
- modification of the nucleic acid sequence to incorporate preferred codons for the host cell;
- extension of the nucleic acid sequence with additional regulation and transcription elements in order to optimize the expression in the host cell.

All further steps in the process for the production of suitable expression vectors and for the expression are state of the art and familiar to a person skilled in the art. Such methods are described for example in Sambrook et al., Molecular Cloning: A Laboratory Manual (1989), Cold Spring Harbor Laboratory Press, New York, USA.

As the fusion peptide is not secreted, it aggregates in the cell, preferably in the cytoplasm. Here the peptide is stored in a compressed and insoluble form (inclusion bodies). This reduces interference with cell functions like proteolytic degradation to a minimum. *Escherichia coli, Streptomyces* or *Bacillus* are for example suitable as prokaryotic host organisms. For the production of the fusion peptides according to the invention the prokaryotes are transformed in the usual manner with the vector which contains the DNA coding for the peptide and subsequently fermented in the usual manner. After lysis of the cells the insoluble inactive peptide (IBs) is isolated in the usual manner for example by centrifugation (pellet fraction). The desired insoluble peptide aggregates can if necessary be further enriched by washing the pellets e.g. with buffers containing detergents.

The insoluble fusion peptide is solubilized preferably with alkaline solutions (e.g., KOH, pH 10) and cleaved by appropriate means, e.g., factor Xa at pH 8.0.

Surprisingly it has turned out that the fusion peptides produced by the process according to the invention are not degraded in the host cells formed as inclusion bodies and, subsequently, can be completely cleaved enzymatically without significant cleavage in the antifusogenic peptide component itself.

Figure 1:
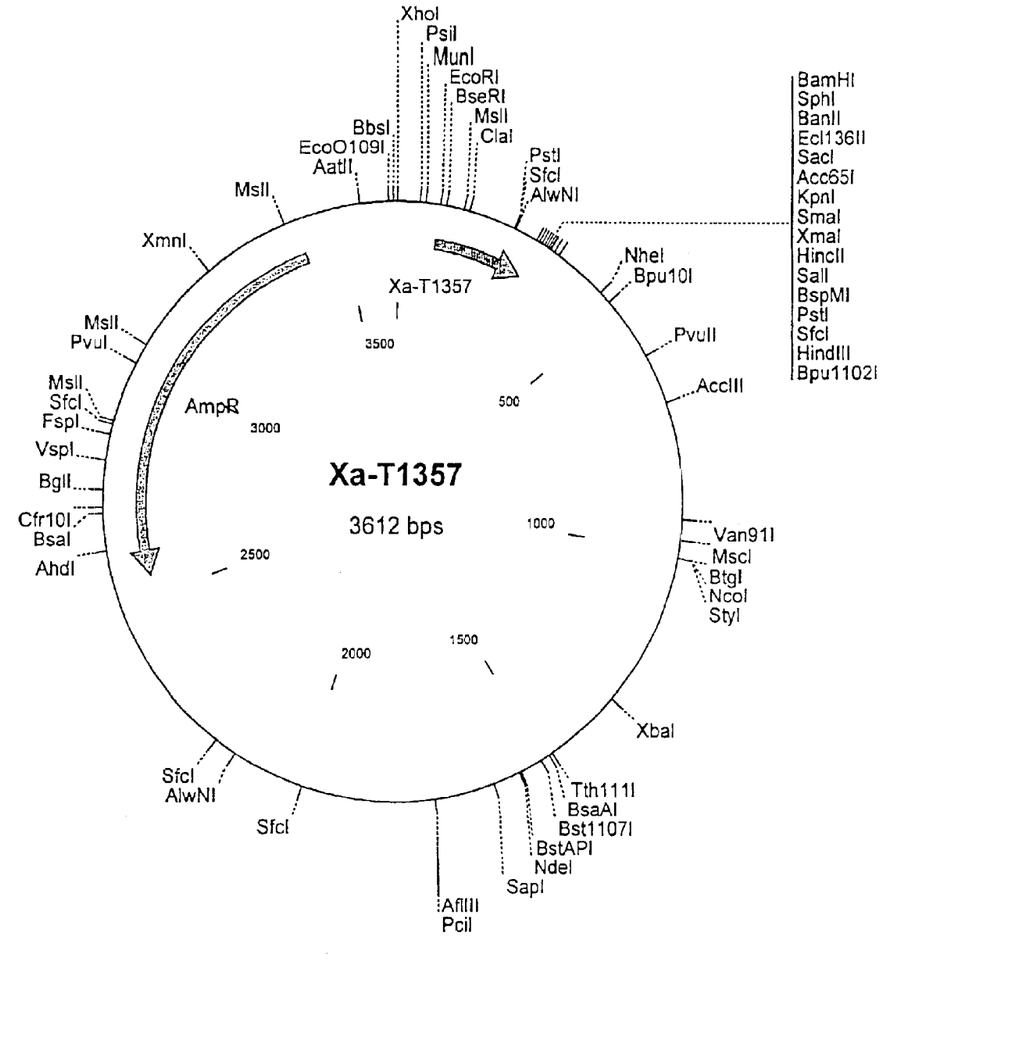
FIG. 1 shows the expression vector encoding Xa-T 1357.

The following examples, references, FIG. 1 and the sequence listing are provided to aid the understanding of the present invention. It is understood that modifications can be made in the procedures set forth without departing from the spirit of the invention.

EXAMPLE 1

Expression Vector Construction

The synthetic gene Xa-T1357 has the following structure (from the N-terminus to the C-terminus):

EcoRI cleavage site
ribosome binding site of phage T5
amino acids M, R, G, S
amino acids 6×H (His-tag)
amino acids A, I, D, V
factor Xa linker I, E, G, R
T1357 sequence (39 amino acids)
amino acid G
2 stop codons
BamHI cleavage site
and is described by SEQ ID NO:1.

The synthetic gene was constructed via gene synthesis with the use of four oligonucleotides consisting of the sequence of the gene with three overlapping regions of 20, 21 and 20 base pairs. Synthesis was performed by means of a two-step PCR reaction. In the first step, oligo 1 and 2 and oligo 3 and 4 each were applied as a template for complete synthesis of the N-terminal portion of the gene and the C-terminal portion of the gene, respectively. The products were used as a template for the second step, whereby equal portions of these products were applied. Primers 1 and 4 were used as the synthesis primers for this step.

The resulting synthetic gene was digested with EcoRI and BamHI, and so was the vector pQE-30 (Qiagen, DE). Both restriction digestions were purified by means of gel extraction (Qiagen) and then used for ligation for the production of an expression vector. The ratio of the insert to the vector was 3:1. The vector is shown in FIG. 1.

The sequence and the correct orientation of the construct were determined by means of restriction control and sequencing (SequiServe, DE).

EXAMPLE 2

Fermentation, IB Isolation and Solubilization

Fermentation and IB Isolation:

*E. coli* cells containing the expression vector of Example 1 are fermented in complex medium, with selection using ampicillin and kanamycin. LB medium is used for the pre-culture. For the main culture, yeast extract is used as the only complex component as the C- and N-source, and glycerine is used as an additional C-source. Both components are added in concentrated form during the fed-batch phase. Expression with IPTG is induced in a suitable growth phase. The pH value is adjusted to 7±0.2 using phosphoric acid/caustic soda. Fermentation is conducted with an overpressure of up to 0.5 bar. The oxygen partial pressure is controlled via the rotational speed of the stirrer, aeration and/or rate of dosage. After growth arrest and after a corresponding period of expression, the biomass is harvested, immediately or after cooling, by centrifugation and is stored in a frozen state.

The foreign protein to be expressed is obtained intracellularly in the form of inclusion bodies (IB), an IB preparation is conducted prior to purification. To this end, the biomass is disrupted with the use of a homogenizer and the IB's are purified in several washing and centrifugation steps.

Solubilization 5.21 g of IB's (prepared from 20 g of cells by high-pressure disruption in 100 ml disruption buffer (100 mM Tris-HCl, 10 mM EDTA, pH 7.0)) are dissolved in 206 ml of 30 mM KOH pH 12 at room temperature, while stirring. Protein content solubilisate: c=3.2 mg/ml (Bradford protein assay, Bradford M. M., Analytical Biochemistry 72 (1976) 248–254)→659.2 mg total protein.

Molecular weight of the fusion peptide of: MW=7161.96 (7156.05 monoisotopic)

The peptides

MRGS-HHHHHH-AIDV-IEGR-*RSV118*-G    (SEQ ID NO:11)

MRGS-HHHHHH-AIDV-IEGR-*MV257*-G    (SEQ ID NO:12)

are produced in the same manner, whereby the sequences RSV 118 and MV 257 (see Table 1) are used instead of the sequence "T 1357".

EXAMPLE 3

Citraconylation and Cleavage a) Citraconylation

For citraconylation there is applied to the fusion peptide a mixture of citraconic acid anhydride (MW: 112.09, p=1.245 g/ml) and dioxane at a ratio of 1:1, whereby the citraconic acid anhydride is used at a 12-fold excess per mole of amino group. For citraconylation 0.66 g fusion peptide (MW: 7162, C=3.2 mg/ml in disruption buffer of Example 2b), five amino groups/molecule and 570 µl citraconic acid anhydride are required. The solubilisate is adjusted to a pH of 11 by using concentrated HCl. Subsequently, a mixture of 570 µl citraconic acid anhydride and 570 µl dioxane is added dropwise and the solution is buffered with 2 M KOH so that the pH value does not drop below 8.5. After adjusting the pH value to pH 10, the preparation is incubated overnight at room temperature, while stirring. The reaction is stopped with ethanol amine (21 ml of 1 M ethanol amine in $H_2O$, pH 8.0) (final concentration of ethanol amine in the solution: 100 mM) and the pH value is adjusted to pH 8.5 by using 2 M HCl. The citraconylated material is then stored at −20° C. Total volume of reaction batch: 237 ml.

b) Cleavage with Trypsin

The reaction batch is mixed with 11.85 ml of 1 M NaCl (final concentration 50 mM) and with 1.25 ml of 1 M $CaCl_2$ (final concentration 2 mM) and batches thereof of 10 ml each are incubated with 1.3 U/ml of trypsin for 80 minutes at room temperature, while stirring. At a level of trypsin of 1.3 U/ml, complete cleavage of the fusion protein has taken place. Cleavage is determined by means of 16%-tricin-SDS gels and HPLC analysis. The trypsin applied is trypsin from Roche Diagnostics GmbH (degree of purity II, 0.0091% chymotrypsin activity, activity: 206 U/ml).

c) Determination of Cleavage by HPLC Analysis

The portion of peptide is determined by HPLC with a linear calibration curve, which was prepared with synthetic Ac-T1357-G-OH. The following HPLC system is used:
Column: Pharmacia Source 15RPC ST 4.6/100
Eluent: buffer A: 20 mM Tris, pH 7.5; buffer B: 70% acetonitrile+30% buffer A
Gradient: in 28 minutes from 0% B to 100% B
Flow: 1 ml/min.
Detection: UV 226 nm

EXAMPLE 4

Purification a) Ammonium Sulfate Precipitation

To the reaction mixture of example 3b solid ammonium sulfate (AS) (final concentration 2 M) is added and, after dissolving the AS, is stirred at room temperature. The precipitated peptide is removed by centrifugation (10,000 rpm) for 5 minutes at 4° C. and the pellet obtained (containing peptide and trypsin) is dissolved in 5 ml Tris buffer (50 mM, pH 8.5).

b) Benzamidine Sepharose 6B Chromatography

Removal of trypsin from the above-described solution is accomplished by means of a benzamidine column.
Application: 5 mg of protein
Column: HR 16 (Pharmacia, h=3.3 cm, d=1.6 cm, V=10 ml)
Material: Benzamidine Sepharose 6B (Pharmacia No. 17-0568-01), regenerated according to the manufacturer's instructions and equilibrated with 50 mM Tris buffer, pH 8.5
Flow: 1 ml/min.
Washing the column: 50 mM Tris buffer, pH. 8.5

40 to 80% of the peptide flows through the column, the rest binds to the column material. In the subsequent elution with 60% of ethanol, a possibly present co-elution of the trypsin cannot be determined because trypsin is no longer detectable when the content of ethanol is 20% or higher. Both in the flow-through and in the elution, the peptide appears as a single peak in the HPLC analysis, and the peptide is also homogeneous in the SDS gel.

c) Purification via Phenyl Sepharose FF

Phenyl Sepharose FastFlow (Pharmacia): 5 mg of the pellet precipitate with AS (protein content c=5 mg/ml) are dissolved in 1 ml Tris buffer (50 mM Tris pH 8.5) and applied to the column. The peptide binds completely to the column material and can be eluted with an ethanol gradient of 20 to 60%, in 50 mM Tris HCl, pH 8.5 the elution taking place over a long period of retention. Peptide fractions are homogeneous.

What is claimed is:

1. A process for the production of an antifusogenic peptide by producing a fusion peptide of a length of from 14 amino acids up to 70 amino acids in a prokaryotic host cell, comprising the steps, under such conditions that inclusion bodies of said fusion peptide are formed, of:
   (a) expressing in said host cell a nucleic acid encoding said fusion peptide consisting of a first peptide which is an antifusogenic peptide of a length of 10 to 50 amino acids and a second peptide of a length of 4 to 30 amino acids, said first peptide being N-terminally linked to said second peptide;
   (b) cultivating said host cell to produce said infusion bodies and;
   (c) recovering said antifusogenic peptide from said inclusion bodies, wherein said recovered antifusogenic peptide consists of said fusion peptide or a peptide comprising the antifusogenic peptide of 10 to 50 amino acids resulting from cleavage of said fusion peptide.

2. The process according to claim 1, wherein the second peptide consists of a peptide selected from:
   (a) peptides which consist of from 4 amino acids to 20 amino acids,
   (b) cleavable peptide linkers which consist of from 4 amino acids to 10 amino acids, and
   (c) peptides consisting of
      (i) a peptide consisting of up to 20 amino acids, and
      (ii) a cleavable peptidic linker which consists of up to 10 amino acids, wherein the cleavable peptide linker is located between the N-terminus of the first peptide and the C-terminus of the peptide according to (i).

3. The process according to claim 1, wherein the ratio of the molecular weight of the first peptide to the molecular weight of the second peptide is from 10:1 to 1:2.

4. The process according to claim 1, further comprising recovering the inclusion bodies produced in accordance with step (a) from said host cells, and solubilizing the recovered inclusion bodies, to recover said antifusogenic peptide from the inclusion bodies.

5. The process according to claim 4, wherein the first peptide is cleaved from the second peptide of the fusion peptide during or after solubilization of the recovered inclusion bodies.

* * * * *

SEQUENCE LISTING

```
<160> NUMBER OF SEQ ID NOS: 20

<210> SEQ ID NO 1
<211> LENGTH: 221
<212> TYPE: DNA
<213> ORGANISM: Artificial Sequence
<220> FEATURE:
<221> NAME/KEY: CDS
<222> LOCATION: (32)..(211)
<223> OTHER INFORMATION: Description of Artificial Sequence: synthetic
      gene Xa-T 1357

<400> SEQUENCE: 1
cgaggaattc attaaagagg agaaattaac t atg aga gga tcg cat cat cat         52
                                  Met Arg Gly Ser His His His
                                    1               5 cat cat cat gct atc gat gtt att gaa ggc cgt tgg cag gaa tgg gaa       100
His His His Ala Ile Asp Val Ile Glu Gly Arg Trp Gln Glu Trp Glu
         10                  15                  20
```

```
cag aaa att acc gcc ctg ctg gaa cag gcg caa att cag caa gag aaa      148
Gln Lys Ile Thr Ala Leu Leu Glu Gln Ala Gln Ile Gln Gln Glu Lys
        25                  30                  35 aac gaa tat gag ctg cag aaa ctg gat aag tgg gcg agc ctg tgg gaa      196
Asn Glu Tyr Glu Leu Gln Lys Leu Asp Lys Trp Ala Ser Leu Trp Glu
 40                  45                  50                  55 tgg ttc ggc taa tga ggatccagct                                       221
Trp Phe Gly
                60

<210> SEQ ID NO 2
<211> LENGTH: 58
<212> TYPE: PRT
<213> ORGANISM: Artificial Sequence
<220> FEATURE:
<223> OTHER INFORMATION: Description of Artificial Sequence: synthetic
      gene  Xa-T 1357

<400> SEQUENCE: 2

Met Arg Gly Ser His His His His His His Ala Ile Asp Val Ile Glu
 1               5                  10                  15

Gly Arg Trp Gln Glu Trp Glu Gln Lys Ile Thr Ala Leu Leu Glu Gln
            20                  25                  30

Ala Gln Ile Gln Gln Glu Lys Asn Glu Tyr Glu Leu Gln Lys Leu Asp
        35                  40                  45

Lys Trp Ala Ser Leu Trp Glu Trp Phe Gly
    50                  55

<210> SEQ ID NO 3
<211> LENGTH: 70
<212> TYPE: DNA
<213> ORGANISM: Artificial Sequence
<220> FEATURE:
<223> OTHER INFORMATION: Description of Artificial Sequence:primer 1

<400> SEQUENCE: 3
cgaggaattc attaaagagg agaaattaac tatgagagga tcgcatcatc atcatcatca    60
tgctatcgat                                                           70

<210> SEQ ID NO 4
<211> LENGTH: 70
<212> TYPE: DNA
<213> ORGANISM: Artificial Sequence
<220> FEATURE:
<223> OTHER INFORMATION: Description of Artificial Sequence:primer 2

<400> SEQUENCE: 4
agcagggcgg taattttctg ttcccattcc tgccaacggc cttcaataac atcgatagca    60
tgatgatgat                                                           70

<210> SEQ ID NO 5
<211> LENGTH: 71
<212> TYPE: DNA
<213> ORGANISM: Artificial Sequence
<220> FEATURE:
<223> OTHER INFORMATION: Description of Artificial Sequence:primer 3

<400> SEQUENCE: 5
acagaaaatt accgccctgc tggaacaggc gcaaattcag caagagaaaa acgaatatga    60
gctgcagaaa c                                                         71
```

```
<210> SEQ ID NO 6
<211> LENGTH: 71
<212> TYPE: DNA
<213> ORGANISM: Artificial Sequence
<220> FEATURE:
<223> OTHER INFORMATION: Description of Artificial Sequence:primer 4

<400> SEQUENCE: 6
agctggatcc tcattagccg aaccattccc acaggctcgc ccacttatcc agtttctgca      60
gctcatattc g                                                          71

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence:peptid T1357

<400> SEQUENCE: 7

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 8
<211> LENGTH: 36
<212> TYPE: PRT
<213> ORGANISM: Artificial Sequence
<220> FEATURE:
<223> OTHER INFORMATION: Description of Artificial Sequence:peptide T680

<400> SEQUENCE: 8

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 9
<211> LENGTH: 35
<212> TYPE: PRT
<213> ORGANISM: Artificial Sequence
<220> FEATURE:
<223> OTHER INFORMATION: Description of Artificial Sequence:peptide
      RSV118

<400> SEQUENCE: 9

Phe Asp Ala Ser Ile Ser Gln Val Asn Glu Lys Ile Asn Gln Ser Leu
 1               5                  10                  15

Ala Phe Ile Arg Lys Ser Asp Glu Leu Leu His Asn Val Asn Ala Gly
            20                  25                  30

Lys Ser Thr
        35

<210> SEQ ID NO 10
<211> LENGTH: 35
<212> TYPE: PRT
<213> ORGANISM: Artificial Sequence
<220> FEATURE:
<223> OTHER INFORMATION: Description of Artificial Sequence:peptide
      MV257
```

```
<400> SEQUENCE: 10

Leu His Arg Ile Asp Leu Gly Pro Pro Ile Ser Leu Glu Arg Leu Asp
 1               5                  10                  15

Val Gly Thr Asn Leu Gly Asn Ala Ile Ala Lys Leu Glu Asp Ala Lys
            20                  25                  30

Glu Leu Leu
        35

<210> SEQ ID NO 11
<211> LENGTH: 54
<212> TYPE: PRT
<213> ORGANISM: Artificial Sequence
<220> FEATURE:
<223> OTHER INFORMATION: Description of Artificial Sequence:peptide
      Xa-RSV118

<400> SEQUENCE: 11

Met Arg Gly Ser His His His His His His Ala Ile Asp Val Ile Glu
 1               5                  10                  15

Gly Arg Phe Asp Ala Ser Ile Ser Gln Val Asn Glu Lys Ile Asn Gln
            20                  25                  30

Ser Leu Ala Phe Ile Arg Lys Ser Asp Glu Leu Leu His Asn Val Asn
        35                  40                  45

Ala Gly Lys Ser Thr Gly
        50

<210> SEQ ID NO 12
<211> LENGTH: 54
<212> TYPE: PRT
<213> ORGANISM: Artificial Sequence
<220> FEATURE:
<223> OTHER INFORMATION: Description of Artificial Sequence:peptide
      Xa-MV257

<400> SEQUENCE: 12

Met Arg Gly Ser His His His His His His Ala Ile Asp Val Ile Glu
 1               5                  10                  15

Gly Arg Leu His Arg Ile Asp Leu Gly Pro Pro Ile Ser Leu Glu Arg
            20                  25                  30

Leu Asp Val Gly Thr Asn Leu Gly Asn Ala Ile Ala Lys Leu Glu Asp
        35                  40                  45

Ala Lys Glu Leu Leu Gly
        50

<210> SEQ ID NO 13
<211> LENGTH: 52
<212> TYPE: PRT
<213> ORGANISM: Artificial Sequence
<220> FEATURE:
<223> OTHER INFORMATION: Description of Artificial Sequence:peptide
      M-HHHHHH-AIDV-IEGR-T1357-G

<400> SEQUENCE: 13

Met His His His His His His Ala Ile Asp Val Ile Glu Gly Arg Tyr
 1               5                  10                  15

Thr Ser Leu Ile His Ser Leu Ile Glu Glu Ser Gln Asn Gln Gln Glu
            20                  25                  30

Lys Asn Glu Gln Glu Leu Leu Glu Leu Asp Lys Trp Ala Ser Leu Trp
        35                  40                  45

Asn Trp Phe Gly
```

<210> SEQ ID NO 14
<211> LENGTH: 51
<212> TYPE: PRT
<213> ORGANISM: Artificial Sequence
<220> FEATURE:
<223> OTHER INFORMATION: Description of Artificial Sequence:peptide
      M-HHHHHH-IEGR-T1357-G

<400> SEQUENCE: 14

Met His His His His His His Ile Glu Gly Arg Trp Gln Glu Trp Glu
 1               5                  10                  15

Gln Lys Ile Thr Ala Leu Leu Glu Gln Ala Gln Ile Gln Gln Glu Lys
            20                  25                  30

Asn Glu Tyr Glu Leu Gln Lys Leu Asp Lys Trp Ala Ser Leu Trp Glu
        35                  40                  45

Trp Phe Gly
        50

<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence:peptide
      M-HHHHHH-IEGR-T680-G

<400> SEQUENCE: 15

Met His His His His His His Ile Glu Gly Arg Tyr Thr Ser Leu Ile
 1               5                  10                  15

His Ser Leu Ile Glu Glu Ser Gln Asn Gln Gln Glu Lys Asn Glu Gln
            20                  25                  30

Glu Leu Leu Glu Leu Asp Lys Trp Ala Ser Leu Trp Asn Trp Phe Gly
        35                  40                  45

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence:peptide
      MR-T1357-G

<400> SEQUENCE: 16

Met Arg Trp Gln Glu Trp Glu Gln Lys Ile Thr Ala Leu Leu Glu Gln
 1               5                  10                  15

Ala Gln Ile Gln Gln Glu Lys Asn Glu Tyr Glu Leu Gln Lys Leu Asp
            20                  25                  30

Lys Trp Ala Ser Leu Trp Glu Trp Phe Gly
        35                  40

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:cleavage
      sequence

<400> SEQUENCE: 17

Asp Asp Asp Asp Lys
 1               5

```
<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:cleavage
      sequence

<400> SEQUENCE: 18

Ile Glu Gly Arg
 1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:cleavage
      sequence

<400> SEQUENCE: 19

Arg Gly Pro Arg
 1

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence:cleavage
      sequence

<400> SEQUENCE: 20

His Pro Phe His Leu Leu Val Tyr
 1               5
```